(12) United States Patent
Mitchek et al.

(10) Patent No.: US 11,014,830 B2
(45) Date of Patent: May 25, 2021

(54) SORBENT COMPOSITIONS FOR THE REMOVAL OF BORON FROM AQUEOUS MEDIUMS

(71) Applicant: ADA Carbon Solutions, LLC, Littleton, CO (US)

(72) Inventors: Micala D. Mitchek, Arvada, CO (US); Roger H. Cayton, Castle Rock, CO (US); Joseph M. Wong, Castle Pines, CO (US); Robert B. Huston, Longmont, CO (US); Lingyan Song, Englewood, CO (US)

(73) Assignee: ADA Carbon Solutions, LLC, Littleton, CO (US)

( * ) Notice: Subject to any disclaimer, the term of this patent is extended or adjusted under 35 U.S.C. 154(b) by 593 days.

(21) Appl. No.: 15/844,074

(22) Filed: Dec. 15, 2017

(65) Prior Publication Data

US 2018/0170773 A1 Jun. 21, 2018

Related U.S. Application Data

(60) Provisional application No. 62/434,901, filed on Dec. 15, 2016.

(51) Int. Cl.
| | |
|---|---|
| *C02F 1/28* | (2006.01) |
| *B01J 20/28* | (2006.01) |
| *B01J 20/32* | (2006.01) |
| *B01J 20/20* | (2006.01) |
| *C07C 31/20* | (2006.01) |
| *C07C 39/08* | (2006.01) |
| *C07C 215/10* | (2006.01) |
| *C07F 1/08* | (2006.01) |
| *C07F 3/04* | (2006.01) |
| *C07F 3/06* | (2006.01) |
| *C07F 5/06* | (2006.01) |
| *C07F 15/02* | (2006.01) |
| *C02F 101/10* | (2006.01) |
| *C02F 103/10* | (2006.01) |
| *C02F 103/34* | (2006.01) |
| *C02F 103/16* | (2006.01) |

(52) U.S. Cl.
CPC ............. *C02F 1/283* (2013.01); *B01J 20/20* (2013.01); *B01J 20/28057* (2013.01); *B01J 20/28076* (2013.01); *B01J 20/327* (2013.01); *B01J 20/3255* (2013.01); *B01J 20/3285* (2013.01); *C02F 1/288* (2013.01); *C07C 31/202* (2013.01); *C07C 31/205* (2013.01); *C07C 39/08* (2013.01); *C07C 215/10* (2013.01); *C07F 1/08* (2013.01); *C07F 3/04* (2013.01); *C07F 3/06* (2013.01); *C07F 5/069* (2013.01); *C07F 15/025* (2013.01); *B01J 2220/50* (2013.01); *C02F 2101/108* (2013.01); *C02F 2103/10* (2013.01); *C02F 2103/16* (2013.01); *C02F 2103/346* (2013.01)

(58) Field of Classification Search
CPC .. C02F 1/28; C02F 1/283; C02F 1/288; C02F 2101/108; C02F 2103/10; C02F 2103/16; C02F 2103/346; B01J 20/20; B01J 20/28057; B01J 20/28076; B01J 20/3255; B01J 20/327; B01J 2220/50; C07C 31/202; C07C 31/205; C07C 39/08; C07C 215/10; C07F 1/08; C07F 3/04; C07F 3/06; C07F 5/069; C07F 15/025
USPC ........................................................ 502/400
See application file for complete search history.

(56) References Cited

U.S. PATENT DOCUMENTS

| | | | |
|---|---|---|---|
| 3,856,670 A | 12/1974 | Peterson | |
| 4,755,298 A | 7/1988 | Grinstead | |
| 6,309,446 B1 * | 10/2001 | Nakanoya | ................ B01J 20/20 502/418 |
| 7,846,339 B2 | 12/2010 | Suzuki et al. | |
| 8,070,950 B2 | 12/2011 | Suzuki | |
| 8,236,180 B2 | 8/2012 | Yubasaki | |
| 8,357,300 B2 | 1/2013 | Roh et al. | |
| 9,314,767 B2 | 4/2016 | McMurray et al. | |
| 9,468,904 B2 | 10/2016 | McMurray et al. | |
| 9,539,538 B2 | 1/2017 | Wong et al. | |
| 9,561,462 B2 | 2/2017 | McMurray et al. | |
| 10,035,126 B2 | 7/2018 | McMurray et al. | |
| 10,137,403 B2 | 11/2018 | McMurray et al. | |
| 10,159,928 B2 | 12/2018 | McMurray | |
| 10,307,706 B2 | 6/2019 | Li et al. | |
| 10,421,037 B2 | 9/2019 | Li et al. | |
| 10,449,492 B2 | 10/2019 | Huston et al. | |
| 10,456,745 B2 | 10/2019 | Huston et al. | |
| 2007/0254807 A1 | 11/2007 | Bisque et al. | |
| 2009/0057231 A1 | 3/2009 | Schelhaas et al. | |
| 2014/0186625 A1 | 7/2014 | Wong et al. | |

(Continued)

OTHER PUBLICATIONS

Choi et al.; "Evaluation of Boron Removal by Adsorption on Solids"; American Chemical Society; vol. 13, No. 2; Feb. 1979; pp. 189-196. Halim et al.; "Boron Removal from Aqueous Solution Using Curcumin-Impregnated Activated Carbon"; Sains Malaysiana 42(9); 2013; pp. 1293-1300.
Ismanto et al.; "Enhanced Boron Adsorption Using PVA-Modified Carbonaceous Materials"; Composite Interfaces; vol. 21, No. 7, 2014; pp. 639-650.

(Continued)

*Primary Examiner* — Edward M Johnson
(74) *Attorney, Agent, or Firm* — Sheridan Ross P.C.

(57) ABSTRACT

Sorbent compositions that include a base sorbent material having a high porosity and surface area and a boron-selective agent are particularly useful for the sequestration of boron from waste materials such as coal combustion residual leachate (CCRs). By using a boron-selective agent in conjunction with a high surface area base sorbent material such as activated carbon or biochar, a sorbent composition with a high capacity for sequestering boron at relatively low cost is provided.

29 Claims, No Drawings

(56) References Cited

U.S. PATENT DOCUMENTS

| | | |
|---|---|---|
| 2015/0165416 A1 | 6/2015 | Wong et al. |
| 2015/0235326 A1 | 8/2015 | Hansen et al. |
| 2016/0214078 A1 | 7/2016 | Li et al. |
| 2016/0296908 A1 | 10/2016 | Li et al. |
| 2017/0043316 A1 | 2/2017 | Li et al. |
| 2017/0043321 A1 | 2/2017 | Li et al. |
| 2018/0001257 A1 | 1/2018 | Wong et al. |
| 2018/0028970 A1 | 2/2018 | Huston et al. |
| 2018/0029006 A1 | 2/2018 | Li et al. |
| 2018/0029008 A1 | 2/2018 | Li et al. |
| 2018/0029009 A1 | 2/2018 | Li et al. |
| 2019/0291041 A1 | 9/2019 | McMurray et al. |
| 2019/0358578 A1 | 11/2019 | McMurray et al. |
| 2020/0001228 A1 | 1/2020 | Li et al. |
| 2020/0047107 A1 | 2/2020 | Cayton |

OTHER PUBLICATIONS

Kluczka et al.; "Boron Removal from Wastewater Using Adsorbents"; Environmental Technology; vol. 28; 2007; pp. 105-113.

Rajakovic et al.; "Soprtion of Boric Acid and Borax by Activated Carbon Impregnated with Various Compounds"; Carbon; vol. 34, No. 6; 1996; pp. 769-774.

Kluczka et al.; "Removal of Boron Dissolved in Water"; Environmental Progress; vol. 26, No. 1; Apr. 2007; pp. 71-77.

U.S. Appl. No. 16/657,634, filed Oct. 18, 2019, Huston et al.
U.S. Appl. No. 16/725,993, filed Dec. 23, 2019, Huston et al.
U.S. Appl. No. 15/930,145, filed May 12, 2020, Li et al.
U.S. Appl. No. 16/911,161, filed Jun. 24, 2020, Wong et al.

\* cited by examiner

SORBENT COMPOSITIONS FOR THE REMOVAL OF BORON FROM AQUEOUS MEDIUMS

CROSS-REFERENCE TO RELATED APPLICATION

This application claims the priority benefit of U.S. Provisional Patent Application No. 62/434,901 filed on Dec. 15, 2016, entitled "SORBENT COMPOSITIONS FOR THE REMOVAL OF BORON FROM AQUEOUS MEDIUMS," which is incorporated herein by reference in its entirety.

FIELD

This disclosure relates to the treatment of aqueous mediums (e.g., waste water, ground water, etc.) to remove boron and/or borates, and relates to sorbent compositions that are useful for such treatment, and to methods for making such sorbent compositions.

BACKGROUND

Regulations for groundwater monitoring and corrective action of coal combustion residuals (CCR, primarily composed of coal ash) landfills and surface impoundments were put in place by the Coal Combustion Residuals Rule (40 CFR Parts 257 and 261) calling for viable remedy options to be made available. Among the elements subject to regulation is boron, which is known to be harmful to animals and humans in elevated concentrations, and may cause gastrointestinal disorders, central nervous system disorders, and the like. Leachate from CCRs commonly include a boron concentration of about 1 ppm to 14 ppm.

The World Health Organization (WHO) limit for boron in drinking water is 2.4 mg/L, and several states have limits ranging from 0.6 mg/L to 1 mg/L. Boron has a high potential for contaminating groundwater at CCR sites because it is the most abundant of the minor elements found in coal ash, is highly mobile in an aqueous environment, and doesn't readily precipitate. It is not typically removed by conventional water treatment methods, and removal requires high-cost methods such as boron specific ion exchange resins, reverse osmosis, and/or electro-deionization. Interest has been focused on the possibility of in-situ, passive treatment, such as permeable reactive barriers, for remediation at CCR landfills and surface impoundments.

A boron specific ion exchange resin is the most widely used selective boron removal technology, but it is limited by the resin's hydrophobicity, moderate surface area, large chemical requirements for regeneration, and high price.

SUMMARY

Existing removal technologies are not readily adaptable for in-situ treatment to remove boron from aqueous mediums, and a need for a long lasting, high capacity, boron sorbent has been recognized. Other industries that also require selective removal of boron from aqueous mediums may also benefit from the sorbents and methods disclosed herein. These include, but are not limited to, flue gas desulfurization waste water, produced water, desalinization, ultra-pure water, agricultural water, geothermal water, and landfill leachate.

The present disclosure provides a sorbent composition having a favorable capacity for removal of boron and/or borates from an aqueous solution. The sorbent composition includes a base sorbent material having a high surface area, such as activated carbon or biochar. A boron-selective agent is combined with (e.g., deposited on) the base sorbent material. By using a boron-selective agent in conjunction with a high surface area base sorbent material such as activated carbon or biochar, a sorbent composition with a high capacity for sequestering boron and a relatively low cost is provided.

In one embodiment, a sorbent composition is disclosed. The sorbent composition includes a base sorbent material and a boron-selective agent that is combined with the base sorbent material. The boron-selective agent is selected to increase the removal of boron from an aqueous medium as compared to the untreated base sorbent material, e.g., as compared to the base sorbent material that has not been combined with the boron-selective agent. By way of example, the base sorbent material may be a high surface area material such as activated carbon, e.g., powdered activated carbon or granulated activated carbon, or biochar. The boron-selective agent may be selected from several compounds (e.g., classes of compounds) that are selected to enhance the sequestration of boron by the base sorbent material, such as by forming stable molecular complexes with the boron.

In another embodiment, a method for the manufacture of a sorbent composition is disclosed, where the method includes contacting a base sorbent material with a boron-selective agent, where the boron-selective agent enhances the removal of boron from an aqueous medium as compared to the untreated base sorbent material. For example, the combining step may include contacting the base sorbent material with a solution comprising the boron-selective agent. In other characterization, the combining step may include admixing particulates of the base sorbent material with particulates of the boron-selective agent.

In another embodiment, a method for reducing the boron concentration in an aqueous medium is disclosed. The method may include contacting an aqueous medium with a base sorbent material in the presence of a boron-selective agent. The boron-selective agent may be combined with the base sorbent material, e.g., before being contacted with the aqueous medium. Alternatively, the boron-selective agent may be dispersed into the aqueous medium before or during contact of the aqueous medium with the base sorbent material.

These and other embodiments and characterizations of a sorbent composition, a method for manufacturing a sorbent composition and a method for using the sorbent composition will become apparent from the following description.

DESCRIPTION OF THE EMBODIMENTS

The present disclosure is directed to sorbent compositions, methods for making the sorbent compositions and methods for using the sorbent compositions, e.g., to selectively remove boron species from an aqueous medium such as wastewater. The sorbent compositions are capable of removing boron species from aqueous mediums and also have a high capacity for boron sequestration (e.g., for boron removal). The sorbent compositions may also be relatively cost-effective as compared to known methods for the removal of boron from aqueous mediums. The boron species sequestered by the sorbent compositions disclosed herein may include elemental boron or borates, for example. Although the following description refers to the removal of boron and the use of a boron selective agent for the sake of convenience, the boron selective agent encompasses those agents that are useful for the sequestration of both elemental boron and/or boron compounds, e.g. ionic compounds such as borates.

Broadly characterized, the sorbent compositions include a combination of a base material (e.g., a base sorbent material) having a relatively high porosity and a high surface area, and a boron-selective agent.

The base sorbent material may advantageously have a high pore volume. In one characterization, the base sorbent material has a total pore volume (sum of micropore volume plus mesopore volume plus macropore volume) of at least about 0.10 cc/g, such as at least 0.20 cc/g, at least about 0.25 cc/g or even at least about 0.30 cc/g. In certain characterizations, the micropore volume of the base sorbent material may be at least about 0.10 cc/g, such as at least about 0.15 cc/g. Further, the mesopore volume (i.e., pores having a diameter of from 20 Å to 500 Å) may be at least about 0.10 cc/g, such as at least about 0.15 cc/g. In one characterization, the ratio of micropore volume (i.e., pores having a diameter of not greater than 20 Å) to mesopore volume in the base sorbent material may be at least about 0.7, such as 0.9, and may be not greater than about 1.5. Such levels of micropore volume relative to mesopore volume may advantageously enable efficient capture and sequestration of boron species (e.g., boron and/or borates) by the base sorbent material. Pore volumes may be measured using gas adsorption techniques (e.g., $N_2$ adsorption) using instruments such as a TriStar II Surface Area Analyzer 3020 or ASAP 2020 (Micromeritics Instruments Corporation, Norcross, Ga., USA).

In another characterization, the base sorbent material has a relatively high surface area. In one characterization, the base sorbent material may have a surface area of at least about 25 $m^2/g$, such as at least about 50 $m^2/g$, and up to about 125 $m^2/g$, such as up to about 100 $m^2/g$. Surface areas in this range may be provided by base sorbent materials such as biochar. For other applications, higher surface area base sorbent materials may be more effective. In one such characterization, the base sorbent material may have a surface area of at least about 350 $m^2/g$, such as at least about 400 $m^2/g$, at least about 500 $m^2/g$, at least about 600 $m^2/g$, or even at least about 1000 $m^2/g$. Such high surface areas may be provided by activated carbons, for example. Surface area may be calculated using the Brunauer-Emmett-Teller (BET) theory or Density Functional Theory (DFT) equation that models the physical adsorption of a monolayer of nitrogen gas molecules on a solid surface and serves as the basis for an analysis technique for the measurement of the specific surface area of a material. BET surface area may be measured using the Micromeritics TriStar II 3020 or ASAP 2020 (Micromeritics Instrument Corporation, Norcross, Ga.).

Useful base sorbent materials may advantageously comprise particles (e.g., free flowing particles) that are highly porous and have a high surface area. For example, the base sorbent material may comprise porous carbonaceous particles, zeolite particles, silica particles (including silica gel), alumina particles (e.g., activated alumina), clay particles (e.g., aluminosilicates) and combinations thereof. In one embodiment, the base sorbent material includes porous carbonaceous particles. Examples of porous carbonaceous particles include activated carbon such as powdered activated carbon (PAC) and/or granular activated carbon (GAC), reactivated carbon, carbonaceous char such as biochar (e.g., a porous material made from biomass by pyrolysis), and combinations thereof. In one particular characterization, the base sorbent material includes activated carbon and/or biochar. In this regard, although the following discussion primarily refers to the use of porous carbonaceous particles as the base sorbent material, specifically activated carbon, the sorbent compositions of the present disclosure are not so limited. The activated carbon may be derived from a variety of sources (e.g., feedstocks), including anthracite coal, bituminous coal, lignite coal, coconut shells, wood, and the like. In one characterization, the activated carbon is derived from a lignite coal feedstock, which generally has a higher mineral ash content than activated carbon derived from anthracite coal.

In certain embodiments, the base sorbent material comprises particles having a relatively small median average particle size (D50), e.g., to enhance the efficiency of boron sequestration by the sorbent composition. In one characterization, the median average particle size of the base sorbent material is not greater than about 100 µm, such as not greater than 75 µm, not greater than 50 µm, such as not greater than about 30 µm, or even not greater than about 25 µm. In some applications, it may be desirable to utilize a base sorbent material having a median average particle size of not greater than about 20 µm, not greater than about 15 µm and even not greater than about 12 µm. Characterized in another way, the median (D50) particle size of the base sorbent material may be at least about 5 µm, such as at least about 6 µm, or even at least about 8 µm. On example of such a base sorbent material is PAC. The D50 median average particle size may be measured using techniques such as light scattering techniques (e.g., using a Saturn DigiSizer II, available from Micromeritics Instrument Corporation, Norcross, Ga.).

Depending upon the application of the sorbent composition, it may be desirable to utilize base sorbent materials having a larger average size, e.g., in the form of agglomerates or aggregates, e.g., granules. For example, the base sorbent material may be in the form of granules having a median size of at least about 0.2 mm, such as at least about 0.3 mm. Typically, the granules will have a median size of not greater than about 3.0 mm, such as not greater than about 2.5 mm. In another characterization, the granules may have a mesh size of about 8×20, about 8×30, or about 20×40 in the Tyler mesh series. In one characterization, the granules comprise activated carbon, i.e., granulated activated carbon ("GAC").

In another example, the base sorbent material may be in the form of extrudates, e.g., pellets that are formed by extrusion or a similar process. For example, the base sorbent material may be in the form of extruded pellets of activated carbon and/or of biochar.

Although free-flowing particles, granules or extrudates of the base sorbent material are described above, the use of larger, rigid or semi-rigid porous bodies (e.g., porous honeycomb structures) that are combined with the boron-selective agent are also contemplated by the present disclosure.

According to an embodiment of the present disclosure, the base sorbent material is combined with a boron-selective agent to form the sorbent composition. There are a wide variety of compounds that are capable of enhancing the boron sequestration of the base sorbent material, e.g. by boron complexation. In one characterization, the boron selective agent comprises a compound that includes a 1,2 hydroxyl, 1,2 carboxyl or 1,2 carbonyl group. Particular examples of such compounds include, but are not limited to, sorbitol, mannitol, polyvinyl alcohol (PVA), 1,2 ethanediol, 1,2 propanediol, catechol, cyclodextrin, tannic acid, glucose, mannose, glycerol, ribose, cellulose, curcumin, citric acid, tartaric acid and malic acid.

The boron-selective agent may also be selected from compounds that include 1,3 hydroxyl, 1,3 carboxyl or 1,3 carbonyl groups. Examples of such compounds include, but are not limited to, salicyl alcohol, 1,3 propanediol, bis (hydroxymethyl)phenol, salicylic acid and dihydroxyl benzonic acid.

The boron-selective agents listed above may also include amino or imino groups. Examples include, but are not limited to, imino bis propylene glycol, n-methyl-glucamine, and octyl-glucamine.

In an aqueous environment, boron is present as a weak Lewis Acid, namely boric acid ($B(OH)_3$), and accepts a hydroxyl ion to form the borate anion (pKa=9.24). While not wishing to be bound by any particular theory, it is believed that boric acid and borate ions form stable complexes in solution with 1,2 or 1,3 hydroxyl (carbonyl or carboxyl) groups that are in the favorable cis conformation for boron coordination. Either neutral boron esters or borate complex anions with a proton as a counter ion are formed. Compounds such as organic acids, alcohols and polyols include this favorable orientation of hydroxyl groups. The addition of an imino or amino group to the polyol, as noted above, may neutralize the proton rejected during borate complex formation. Thus, these compounds or derivatives of these compounds may be used as the boron selective agent with the base sorbent material to form a boron-specific sorbent composition.

The removal of boron and/or borates from an aqueous medium may also be facilitated by the use of divalent or trivalent ions present on the base sorbent surface or in the waste stream. Examples include, but are not limited to, $Ca^{2+}$, $Cu^{2+}$, $Zn^{2+}$, $Fe^{2+}$, $Fe^{3+}$, and $Al^{3+}$. For example, salts that are soluble in the waste stream (e.g., chloride salts) may be combined with the sorbent composition, and/or may be added to the waste stream to provide the ions in solution. Such cations may react with the boron species in or on the pores of the base sorbent material. The sorbent composition may be formed such that the salt forms an immobilized cation on the sorbent surface (e.g., on the carbon surface) that may form a complex with the boron in the form of a precipitate that may be separated from the aqueous medium.

The removal of boron and borates may also be facilitated by the use of surfactants as the boron-selective agent, either alone or in combination with one or more of the compounds described above. Useful surfactants may include those with charge classification as anionic, cationic, nonionic or amphoteric. By way of example, cationic salts may enable ion displacement of the cation of the surfactant and reaction with the boron species to form a new compound that can be removed from the liquid stream. Examples of such cationic salts include, but are not limited to, quaternary ammonium salts such as quaternary ammonium chlorides, quaternary ammonium bromides and quaternary ammonium methyl sulfates. Additionally, amphoteric salts may be useful to change the ion characteristics based on the pH and ions present in a solution, thus allowing reaction with the boron species to form a new compound that can be removed. Examples of such amphoteric salts include, but are not limited to, those containing nitrogen such as alkyl amidopropyl betaines, alky ampho acetates and alky ampho propionates. Further, cationic and amphoteric surfactants may also function as a flocculent that increase the molecular weight of the boron species being removed. Anionic and nonionic surfactants can also enable the dispersion of borates to facilitate transfer into the porous regions of the sorbent material.

The sorbent composition comprises an effective amount of one or more of the boron-selective agent(s) to effectuate the removal of boron and/or borates from a fluid such as an aqueous (water-based) medium. In one characterization, the sorbent composition comprises at least about 0.1 wt. % of a boron-selective agent, such as at least about 1 wt. % of a boron-selective agent, such as at least about 3 wt. % of a boron-selective agent, or at least about 5 wt. % of a boron-selective agent. However, too high of a concentration of the boron-selective agent may not increase the capacity or efficiency of boron sequestration, and may even be detrimental. In once characterization, the concentration of a boron-selective agent in the sorbent composition is not greater than about 50 wt. %, such as not greater than about 30 wt. %, such as not greater than about 20 wt. %, or even not greater than about 10 wt. %.

Various techniques may be used to combine the base sorbent material with the boron-selective agent. For example, the boron-selective agent will typically be in the form of a solution and/or slurry, such as by dissolving the boron-selective agent in water. The solution and/or slurry may then be brought into contact with the base sorbent material to coat and/or impregnate the base sorbent material with the solution and/or slurry. One such technique is the incipient wetness technique, wherein the solution is drawn into the pores of the base sorbent material via capillary action. Other techniques include spraying the boron-selective agent solution and/or slurry onto the base sorbent material, impregnating the base sorbent material by soaking it in the solution and/or slurry followed by washing steps, reacting the boron-selective agent to the surface of the base sorbent material, or immobilizing the boron-selective agent on the base sorbent material's surface. Another technique involves injecting the boron-selective agent into the liquid, where it would form complexes with the boron in solution to subsequently be absorbed by the base sorbent material. In any case, the solution may be dried, if necessary, to remove excess liquid and/or to crystallize the boron-selective agent.

In an alternative embodiment, the boron-selective agent may be provided in a substantially dry form (e.g., as particulates) and may be admixed with the base sorbent material, such as by combining the two particular components in a mill or in a mixing unit.

In one embodiment, the base sorbent material may be treated before (pretreated) or after being combined with the boron-selective agent. For example, the base sorbent material may be pretreated by contacting the base sorbent material with a base or an acid (e.g., $HNO_3$). A base may facilitate the attachment of the boron-selective agent (e.g., tartaric acid) to the base sorbent material. In another example, the base sorbent material may be treated by ozonating the surface of the base sorbent material, i.e., by contacting the base sorbent material with an effective amount of ozone. Ozone treatment may advantageously place oxygen groups on the base sorbent material surface (e.g., carbon surface) that have an affinity for the boron species, e.g., for boric acid.

Another embodiment of the present disclosure is directed to methods for the removal and/or sequestration of boron (e.g, boron or other boron species such as borates), particularly for the removal of boron from aqueous (water-based) mediums. Such aqueous mediums may include, but are not limited to, waste streams from CCR landfills, metal fabrication and processing (e.g., electroplating), electrical component manufacture, and the like. Other aqueous streams that include elevated levels of boron include the desalinated water from desalinization plants utilizing reverse osmosis and geothermal water.

To facilitate the removal of boron from an aqueous medium, the method includes contacting the aqueous medium with a base sorbent material in the presence of a boron-selective agent. The boron-selective agent may be combined with the base sorbent material, e.g., before being contacted with the aqueous medium, as is discussed above. Alternatively, the boron-selective agent may be dispersed into the aqueous medium before or during contact of the aqueous medium with the base sorbent material, e.g, with a base sorbent material that has not been combined with the boron-selective agent.

As is known to those of skill in the art, the sorbent compositions including the base sorbent and the boron-selective agent may be contacted with the aqueous medium (e.g., waste stream) to remove boron in a wide variety of ways. For example, the sorbent composition may be placed in a cartridge or similar structure through which the aqueous medium flows. In another example, the sorbent composition may be placed on or within a membrane (e.g., a planar membrane) through which the aqueous medium flows. The sorbent composition may also be shaped into an integral structure (e.g., a honeycomb structure, porous carbon blocks) or may be incorporated into such a structure (e.g., a ceramic honeycomb structure). The sorbent composition may also be used in a permeable reactive barrier, such as where the sorbent composition is either buried in a trench or is injected into the subsurface to treat contaminated groundwater.

In certain characterizations, the sorbent compositions disclosed herein have a relatively high capacity for boron removal. In one embodiment, the sorbent compositions have a capacity to capture at least about 1 mg boron per gram of sorbent composition (mg B/g), such as at least about 2 mg B/g, at least about 5 mg B/g, at least about 7.5 mg B/g, at least about 10 mg B/g, at least about 15 mg B/g, or even at least about 20 mg B/g.

In a further characterization, the sorbent composition may advantageously capture (e.g., sequester) the boron in the presence of other contaminants. Merely by way of example, the sorbent composition may be useful for the treatment of CCRs including other contaminants such as those listed in Table I below:

TABLE I

| CCR Constituents | | | | |
|---|---|---|---|---|
| | Starting Leachate Contaminant Level [mg/L] | | | Target Contaminant Level [mg/L] MCL |
| Constituent | Median | 90th Percentile | Maximum | (health based) or SMCL/State limit |
| Boron | 2.6 | 14 | 112 | 0.6-1 |
| Calcium | | | | |
| Chloride | 28 | 74 | 2330 | 200-250 |
| Fluoride | 0.163 | 1.312 | 8.85 | 4 |
| Sulfate | 485 | 1613 | 30500 | 250-400 |
| Total Dissolved Solids | | | | 500 |
| pH (field) | | | | |
| Antimony | 0.002 | 0.02 | 0.59 | 0.006 |
| Arsenic | 0.026 | 0.178 | 1.38 | 0.01 |
| Barium | 0.089 | 0.25 | 0.657 | 2 |
| Beryllium | BDL | BDL | 0.009 | 0.004 |
| Cadmium | 0.002 | 0.013 | 0.065 | 0.005 |
| Chromium | 0.001 | 0.025 | 5.1 | 0.1 |
| Cobalt | | | | |
| Lead | BDL | 0.0004 | 0.008 | 0.015 |
| Lithium | 0.15 | 0.43 | 23.6 | 0.17 |
| Mercury | 4E−06 | 0.000029 | 0.000079 | 0.002 |
| Molybdenum | 0.36 | 1.39 | 60.8 | 0.35-0.73 |
| Selenium | 0.018 | 0.181 | 2.36 | 0.05 |
| Thallium | BDL | 0.005 | 0.018 | 0.002 |
| Fluoride | 0.163 (lab) | 1.312 (lab) | 8.85 (lab) | 4 |
| Radium 226 & 228 | | | | 5 pCi/L |

The sorbent compositions of the present disclosure may be formulated to remove boron even when the boron is present with such other contaminants, such as in a CCR waste stream. In another characterization, the sorbent composition may be formulated to enable one or more of the other contaminant elements to be captured with the boron. For example, the sorbent composition may be formulated to also remove elements such as selenium and/or arsenic from the aqueous medium, along with the boron species.

EXAMPLES

Example 1

Comparative Sample A is comprised of a granular activated carbon (GAC) derived from bituminous coal feedstock. The GAC is characterized as having a mesh size of 8×30, a surface area of at least about 350 $m^2/g$, and a total pore volume of at least about 0.3 cc/g. A batch test is used to evaluate the ability of the sorbent to remove boron from an aqueous solution. Carbon is dosed into a standard solution containing 10 ppm boron, and the mixture is stirred for about 24 hours at room temperature. The solution is then vacuum filtered and analyzed for total boron content via inductively coupled plasma (ICP). The result, expressed as percent boron removed from solution, is expressed in Table II.

Example 2

Comparative Sample B is made by grinding Comparative Sample A down to a powder using a lab-scale disk mill followed by a lab-scale jet mill. Comparative Sample B is characterized as having a median particle size (D50) of about 12 μm. The ability to remove boron is assessed using a batch test and the result is expressed in Table II as percent boron removed from solution.

Example 3

To test for enhanced boron removal, Sample C is formed by adding a diol functionality (N-Methyl-D-Glucamine) to comparative Sample B. The first step in preparation is to dissolve 3.4 g of N-Methyl-D-Glucamine in 5.1 g of deionized water. 4.25 g of this solution is sprayed onto 8.3 g of Sample B while fluidizing the PAC in a mixer for 10 minutes to yield Sample C containing about 17 wt. % N-Methyl-D-Glucamine. The ability to remove boron is assessed using a batch test and the result is expressed in Table II as percent boron removed from solution.

Example 4

To test for enhanced boron removal, Sample D is formed by adding a diol functionality (N-Methyl-D-Glucamine) to comparative Sample B. For preparation, 1.7 g of N-Methyl-D-Glucamine and 8.3 g of Sample B are mixed in a fluidizing mixer for 10 minutes to yield Sample D which contains about 17 wt. % N-Methyl-D-Glucamine. The ability to remove boron is assessed using a batch test and the result is expressed in Table II as percent boron removed from solution.

Example 5

To test for enhanced boron removal, Sample E is formed by adding a diol functionality (sorbitol) to comparative Sample B. The first step in preparation is to dissolve 3.4 g of sorbitol in 5.1 g of deionized water. 4.25 g of this solution is sprayed onto 8.3 g of Sample B while fluidizing the PAC in a mixer for 10 minutes to yield Sample E which contains about 17 wt. % sorbitol. The ability to remove boron is assessed using a batch test and the result is expressed in Table II as percent boron removed from solution.

Example 7

To test for enhanced boron removal, Sample F is formed by adding a diol functionality (sorbitol) to comparative Sample B. For preparation, 1.7 g of sorbitol and 8.3 g of sample B are mixed in a fluidizing mixer for 10 minutes to yield Sample F which contains about 17 wt. % sorbitol. The ability to remove boron is assessed using a batch test and the result is expressed in Table II as percent boron removed from solution.

Example 8

To test for enhanced boron removal, Sample G is formed by adding a diol functionality (sorbitol) to comparative Sample A. For preparation, 1.7 g of sorbitol and 8.3 g of Sample A are mixed in a fluidizing mixer for 10 minutes to yield Sample G which contains about 17 wt. % sorbitol. The ability to remove boron is assessed using a batch test and the result is expressed in Table II as percent boron removed from solution.

TABLE II

Results for Boron Removal

| Sample | Base Sorbent Material | Additive (wt. %) | Additive | Application Method | Dosage (wt. %) | Boron Removal (%) |
|---|---|---|---|---|---|---|
| A* | GAC | 0 | — | — | 0.5 | 28 |
| B* | PAC | 0 | — | — | 0.5 | 34 |
| C | PAC | 17 | Methyl Glucamine | Solution | 0.5 | 49 |
| D | PAC | 17 | Methyl Glucamine | Dry add mix | 0.6 | 60 |
| E | PAC | 17 | Sorbitol | Solution | 0.5 | 62 |
| F | PAC | 17 | Sorbitol | Dry add mix | 0.6 | 76 |
| G | GAC | 17 | Sorbitol | Dry add mix | 0.6 | 70 |

*comparative sample

While various embodiments of a sorbent composition, a method for the manufacture of a sorbent composition and a method for removing boron from an aqueous medium have been described in detail, it is apparent that modifications and adaptations of those embodiments will occur to those skilled in the art. However, it is to be expressly understood that such modifications and adaptations are within the spirit and scope of the present disclosure.

What is claimed is:

1. A sorbent composition comprising a base sorbent material selected from the group consisting essentially of activated carbon, biochar, alumina, silica, clays, zeolites, and combinations thereof and a boron-selective agent that is combined with the base sorbent material, wherein the boron-selective agent increases removal of boron from an aqueous medium as compared to an untreated base sorbent material,
wherein the boron-selective agent comprises a compound selected from the group of compounds comprising 1,2 hydroxyl groups, 1,2 carboxyl groups, 1,2 carbonyl groups, 1,3 hydroxyl groups, 1,3 carboxyl groups, 1,3 carbonyl groups, and combinations thereof.

2. The sorbent composition recited in claim 1, wherein the base sorbent material has a total pore volume of at least about 0.10 cc/g.

3. The sorbent composition recited in claim 1, wherein the base sorbent material has a surface area of at least about 50 m$^2$/g.

4. The sorbent composition recited in claim 1, wherein the base sorbent material comprises activated carbon.

5. The sorbent composition recited in claim 1, wherein the base sorbent material comprises biochar.

6. The sorbent composition recited in claim 1, wherein the boron-selective agent comprises a compound selected from the group of compounds comprising 1,2 hydroxyl groups, 1,2 carboxyl groups, 1,2 carbonyl groups, and combinations thereof.

7. The sorbent composition recited in claim 6, wherein the boron-selective agent comprises a compound selected from the group consisting of sorbitol, mannitol, polyvinyl alcohol (PVA), 1,2 ethanediol, 1,2 propanediol, catechol, tannic acid, glucose, mannose, glycerol, ribose, cellulose, curcumin, citric acid, tartaric acid, malic acid, and combinations thereof.

8. The sorbent composition recited in claim 1, wherein the boron-selective agent comprises a compound selected from the group consisting of compounds comprising 1,3 hydroxyl groups, 1,3 carboxyl groups, 1,3 carbonyl groups, and combinations thereof.

9. The sorbent composition recited in claim 8, wherein the boron-selective agent comprises a compound selected from the group consisting of salicyl alcohol, 1,3 propanediol, bis(hydroxymethyl)phenol, salicylic acid, dihydroxyl benzonic acid, and combinations thereof.

10. The sorbent composition recited in claim 1, wherein the boron-selective agent comprises a functional group that is selected to neutralize a displaced hydrogen atom during boron complexation.

11. The sorbent composition recited in claim 10, wherein the functional group is selected from the group consisting of an imino group, an amino group, and combinations thereof.

12. The sorbent composition recited in claim 11, wherein the boron-selective agent comprises a compound selected from the group consisting of imino bis propylene glycol, methyl-glucamine, octyl-glucamine, and combinations thereof.

13. The sorbent composition recited in claim 1, wherein the boron-selective agent comprises a divalent or trivalent cationic salt, wherein the cation in the divalent or trivalent cationic salt is selected from the group consisting of $Ca^{2+}$, $Cu^{2+}$, $Zn^{2+}$, $Fe^{2+}$, $Fe^{3+}$, $Al^{3+}$, and combinations thereof.

14. The sorbent composition recited in claim 1, wherein the boron-selective agent comprises a surfactant.

15. A sorbent composition comprising:
a base sorbent material selected from the group consisting of activated carbon, biochar, and combinations thereof; and
a boron-selective agent that is combined with the base sorbent material, wherein the boron-selective agent comprises a compound selected from the group of compounds comprising 1,2 hydroxyl groups, 1,2 carboxyl groups, 1,2 carbonyl groups, 1,3 hydroxyl groups, 1,3 carboxyl groups, 1,3 carbonyl groups, and combinations thereof.

16. The sorbent composition recited in claim 15, wherein the base sorbent material has a total pore volume of at least about 0.10 cc/g and a surface area of at least about 50 m²/g.

17. A sorbent composition comprising:
a base sorbent material selected from the group consisting of activated carbon, biochar, and combinations thereof and having a total pore volume of at least about 0.10 cc/g, a ratio of micropore volume to mesopore volume of at least about 0.7 and not greater than about 1.5, and a surface area of at least about 50 m²/g; and
a boron-selective agent that is combined with the base sorbent material, wherein the boron-selective agent is present in an amount of at least about 0.1 wt. % to less than about 50 wt. % of the sorbent composition and comprises a compound selected from the group of compounds comprising 1,2 hydroxyl groups, 1,2 carboxyl groups, 1,2 carbonyl groups, 1,3 hydroxyl groups, 1,3 carboxyl groups, 1,3 carbonyl groups, and combinations thereof,
wherein the boron-selective agent increases removal of one or more of elemental boron, a borate, and boric acid from an aqueous medium as compared to an untreated base sorbent material lacking the boron-selective agent.

18. The sorbent composition recited in claim 1, wherein the boron-selective agent is present in an amount of at least about 0.1 wt. % and less than about 50 wt. % of the sorbent composition.

19. The sorbent composition recited in claim 1, wherein the boron-selective agent is present in an amount of at least about 1 wt. % of the sorbent composition.

20. The sorbent composition recited in claim 1, wherein the boron-selective agent is present in an amount of less than 30 wt. % of the sorbent composition.

21. The sorbent composition recited in claim 1, wherein the base sorbent material has a medium average particle size ($D_{50}$) of less than about 100 μm.

22. The sorbent composition recited in claim 1, wherein the base sorbent material has a medium average particle size ($D_{50}$) of less than about 25 μm.

23. The sorbent composition recited in claim 1, wherein the base sorbent material has a ratio of micropore volume to mesopore volume of at least about 0.7 and not greater than about 1.5.

24. The sorbent composition recited in claim 1, wherein the base sorbent material is in a form of a granule having a median size of at least about 0.2 mm and less than about 3.0 mm.

25. The sorbent composition recited in claim 1, wherein the boron is one or more of elemental boron, a borate, and boric acid.

26. The sorbent composition recited in claim 1, wherein the sorbent composition has a capacity to capture at least 1 mg boron per gram of the sorbent composition.

27. The sorbent composition recited in claim 1, wherein the sorbent composition has a capacity to capture at least 20 mg boron per gram of the sorbent composition.

28. The sorbent composition recited in claim 15, wherein the boron-selective agent comprises a compound selected from the group consisting of sorbitol, mannitol, polyvinyl alcohol (PVA), 1,2 ethanediol, 1,2 propanediol, catechol, tannic acid, glucose, mannose, glycerol, ribose, cellulose, curcumin, citric acid, tartaric acid, malic acid, salicyl alcohol, 1,3 propanediol, bis(hydroxymethyl)phenol, salicylic acid, dihydroxyl benzonic acid, sorbitol, and combinations thereof.

29. The sorbent composition recited in claim 17, wherein the boron-selective agent comprises a compound selected from the group consisting of sorbitol, mannitol, polyvinyl alcohol (PVA), 1,2 ethanediol, 1,2 propanediol, catechol, tannic acid, glucose, mannose, glycerol, ribose, cellulose, curcumin, citric acid, tartaric acid, malic acid, salicyl alcohol, 1,3 propanediol, bis(hydroxymethyl)phenol, salicylic acid, dihydroxyl benzonic acid, sorbitol, and combinations thereof.

* * * * *